United States Patent
Torabi (10) Patent No.: US 12,144,575 B2
(45) Date of Patent: *Nov. 19, 2024

(54) SURGEON DISENGAGEMENT DETECTION DURING TERMINATION OF TELEOPERATION

(71) Applicant: Verb Surgical Inc., Santa Clara, CA (US)

(72) Inventor: Meysam Torabi, Union City, CA (US)

(73) Assignee: Verb Surgical Inc., Santa Clara, CA (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/977,425

(22) Filed: Oct. 31, 2022

(65) Prior Publication Data
US 2023/0127035 A1  Apr. 27, 2023

(51) Int. Cl.
*A61B 34/00* (2016.01)
*A61B 34/35* (2016.01)
*A61B 17/00* (2006.01)

(52) U.S. Cl.
CPC .............. *A61B 34/75* (2016.02); *A61B 34/35* (2016.02); *A61B 2017/00216* (2013.01); *A61B 2034/742* (2016.02)

(58) Field of Classification Search
CPC ... A61B 34/75; A61B 34/35; A61B 2034/742; A61B 2017/00216; A61B 34/30;
(Continued)

(56) References Cited

U.S. PATENT DOCUMENTS 11,204,640 B2   12/2021   Freiin von Kapri et al.
11,337,767 B2   5/2022    Savall et al.
(Continued)

FOREIGN PATENT DOCUMENTS

WO   WO2017210101   12/2017
WO   WO2019099346   5/2019
(Continued)

OTHER PUBLICATIONS

Homa, et al., "Targeted Attacks on Teleoperated Surgical Robots: Dynamic Model-based Detection and Mitigation", Sep. 29, 2016, Proceedings—46th Annual IEEE/IFIP International Conference on Dependable Systems and Networks, DSN 2016, Institute of Electrical and Electronics Engineers Inc., pp. 395-406.
(Continued)

*Primary Examiner* — Aaron F Roane
(74) *Attorney, Agent, or Firm* — Aikin & Gallant, LLP (57) ABSTRACT

A method for disengagement detection of a surgical instrument of a surgical robotic system, the method comprising: determining whether a user's head is unstable prior to disengagement of a teleoperation mode; determining whether a pressure release has occurred relative to at least one of a first user input device or a second user input device for controlling a surgical instrument of the surgical robotic system during the teleoperation mode; and in response to determining the user's head is unstable or determining the pressure release has occurred, determining whether a distance change between the first user input device and the second user input device indicates the user is performing an unintended action prior to disengagement of the teleoperation mode.

20 Claims, 5 Drawing Sheets

(58) Field of Classification Search
CPC ... A61B 34/37; A61B 2090/502; A61B 34/20; A61B 34/74; A61B 34/76; A61B 34/77; A61B 2017/00207; A61B 2034/2048; A61B 2034/2055; A61B 2090/371; A61B 90/03; B25J 13/02; G16H 20/40; G16H 40/63
USPC .......................................................... 606/1
See application file for complete search history.

(56) References Cited

U.S. PATENT DOCUMENTS

| | | | |
|---|---|---|---|
| 11,571,269 B2* | 2/2023 | Torabi | A61B 34/35 |
| 2003/0060927 A1 | 3/2003 | Gerbi et al. | |
| 2013/0030571 A1 | 1/2013 | Ruiz Morales et al. | |
| 2014/0005683 A1 | 1/2014 | Stand et al. | |
| 2014/0024889 A1 | 1/2014 | Xiaoli | |
| 2017/0319284 A1 | 11/2017 | Itkowitz et al. | |
| 2018/0036088 A1 | 2/2018 | Kilroy et al. | |
| 2018/0078319 A1* | 3/2018 | Nobles | A61B 34/74 |
| 2018/0080841 A1* | 3/2018 | Cordoba | A61B 34/35 |
| 2019/0254754 A1* | 8/2019 | Johnson | G06T 19/006 |
| 2020/0188146 A1* | 6/2020 | Ta | A61F 2/89 |
| 2020/0261160 A1* | 8/2020 | Peine | A61B 34/37 |
| 2021/0030498 A1* | 2/2021 | Peine | A61B 34/74 |

FOREIGN PATENT DOCUMENTS

| | | |
|---|---|---|
| WO | WO2019099504 | 5/2019 |
| WO | WO2019152771 | 8/2019 |

OTHER PUBLICATIONS

International Search Report and Written Opinion for International Application No. PCT/US2020/023208 mailed Nov. 23, 2020, 12 pages.

International Preliminary Report on Patentability for International Application No. PCT/US2020/023208 mailed Sep. 22, 2022, 11 pages.

* cited by examiner

SURGEON DISENGAGEMENT DETECTION DURING TERMINATION OF TELEOPERATION

CROSS-REFERENCE TO RELATED APPLICATIONS

This application is a continuation of pending U.S. application Ser. No. 16/815,748 filed Mar. 11, 2020, which is incorporated herein in its entirety.

FIELD

Embodiments related to surgical robotic systems, are disclosed. More particularly, embodiments related to detection of user disengagements to prevent unintended motions, are disclosed.

BACKGROUND

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to command a robotically-assisted tool located at an operating table. Such operation of a robotically-assisted tool remotely by a surgeon may be commonly referred to as teleoperation. For example, the surgeon may use a computer console located in the operating room, or it may be located in a different city, to command a robot to manipulate the surgical tool mounted on the operating table. The robotically-controlled surgical tool can be an endoscope mounted on a robotic arm. Accordingly, the surgical robotic system may be used by the remote surgeon to perform an endoscopic surgery.

The surgeon may provide input commands to the surgical robotic system, and one or more processors of the surgical robotic system can control system components in response to the input commands. For example, the surgeon may hold in her hand a user input device such as a joystick or a computer mouse that she manipulates to generate control signals to cause motion of the surgical robotic system components, e.g., an actuator, a robotic arm, and/or a surgical tool of the robotic system.

SUMMARY

During teleoperation with an open display in which the user can view their surroundings (as compared to a periscope type display) there is the possibility that the surgeon is looking away from the screen but still holding the user input devices that control the robotic tools. This introduces a chance that when the surgeon is moving the user input devices to, for example dock the devices, the movement could unintentionally move the surgical tools. It is therefore necessary to afford the user with a way to begin (e.g., engage) and end (e.g., disengage) control of the surgical instrument (e.g., a surgical tool) with the hand and foot controls (e.g., a user input device) without unintended movement of the instrument. For example, the user may be required to perform at least one predetermined intentional action before the system will engage and/or disengage teleoperation. For example, docking the user input devices may be an intentional action that is detected by the system and causes the system to pause or disengage the teleoperation mode. Prior to detection of this intentional action, however, the user may also engage in an unintended or unintentional action that is not intended to cause movement of the surgical instrument. For example, prior to docking of the user input device (e.g., the intentional action), the user may begin to move their hands away from one another (toward the docking stations) while holding the user input devices. Since this movement occurs prior to docking, the system may still be engaged and this movement could cause an unintended movement of the associated surgical instrument.

The system therefore also includes a process for detecting these unintended or unintentional actions that may occur prior to, or while initiating, the intentional action, so that the system can prevent the unintended action from causing movement of the surgical instrument. For example, when one or more unintended actions are detected, the system may detect these as pre-disengagement operations and pause or disengage the teleoperation mode. For example, the system may be able to detect these unintended actions occurring before the docking event (e.g., positioning the user input device in a docking station) in a fraction of a second. The system may do this by performing an on-going verification process which includes monitoring, collecting and analyzing data relating to these actions, or characteristics associated with these actions, to determine and confirm an unintended action is occurring. For example, by detecting and analyzing the angular and positional velocity, acceleration and jerk of a signal corresponding to a movement of a user input devices, and comparing the range of motions of left and right user input devices, an unintended action prior to a docking event (that indicates the user disengagement) can be detected. The instant invention can therefore prevent significant unintended tool motion in the abdomen during robotic surgery. Representatively, in one aspect, the disengagement detection operation includes three main parameters that are monitored as follows: (1) head instability; (2) engagement of the user input devices (e.g., based on the detection of user squeezing the user input devices); and (3) a distance between the user input devices (e.g., detection of a distance change greater than, or faster than, a predetermined threshold). Each of these parameters or characteristics may be continually monitored and analyzed to determine whether they suggest the user's action is not intended for controlling the surgical tool and teleoperation should therefore be disengaged.

Representatively, in one aspect, a process for disengagement detection of a surgical instrument of a surgical robotic system including determining whether a user's head is unstable prior to disengagement of a teleoperation mode; determining whether a pressure release has occurred relative to at least one of a first user input device or a second user input device for controlling a surgical instrument of the surgical robotic system during the teleoperation mode; and in response to determining the user's head is unstable or determining the pressure release has occurred, determining whether a distance change between the first user input device and the second user input device indicates the user is performing an unintended action prior to disengagement of the teleoperation mode. In some aspects, the user's head is determined to be unstable if a movement of the user's head is detected by a head tracking device. Still further, determining whether a pressure release has occurred may include detecting an absence of pressure on the user input device by a pressure sensor. In addition, the distance change indicates the user is performing an unintended action when an associated position change exceeds a predetermined disengagement threshold. In some aspects, determining the distance change exceeds the predetermined disengagement threshold includes determining at least one of a velocity, an acceleration and a jerk of the first user input device or the second user input device, and comparing the velocity, the acceleration and the jerk to the predetermined disengagement threshold. In some cases, determining the distance exceeds the predetermined disengagement threshold comprises determining a velocity, an acceleration and a jerk of the first user input device or the second user input device, and comparing the velocity, the acceleration and the jerk to the predetermined disengagement threshold. In still further aspects, the predetermined disengagement threshold may include a velocity threshold, an acceleration threshold and a jerk threshold that correspond to a maximum velocity, a maximum acceleration and a maximum jerk occurring during a teleoperation mode, respectively. In some aspects, determining the distance change further comprises comparing a velocity of the first user input device and a velocity of the second user input device, and when the velocities are the same, determining the position change indicates an unintended user action. In addition, the process may further include, in response to determining the user is performing an unintended action prior to disengagement of the teleoperation mode, disengage the teleoperation mode such that the first user input device and the second user input device are prevented from controlling the surgical instrument. In some aspects, the unintended action prior to disengagement of the teleoperation mode comprises an action by the user relative to the first user input device or the second user input device that is not intended to cause a movement of the associated surgical instrument.

In another aspect, a process for disengagement detection of a surgical instrument of a surgical robotic system may include detecting a first pre-disengagement action that corresponds to a user action prior to disengagement of a teleoperation mode, wherein the first pre-disengagement action indicates a user's head is unstable or a pressure applied to a first user input device is released; in response to detecting the first pre-disengagement action, detecting a second pre-disengagement input that indicates a distance change relative to a first user input device and a second user input device; in response to detecting the second pre-disengagement action, determine whether a position change of at least one of the first user input device or the second user input device associated with the distance change indicates the user action is an unintended pre-disengagement action; and in response to determining the user action is an unintended pre-disengagement action, disengage the teleoperation mode such that the first user input device and the second user input device are prevented from controlling the surgical instrument. In some aspects, the first pre-disengagement input indicates a user's head is unstable if a movement of the user's head is detected. In still further aspects, the first pre-disengagement action indicates a user's head is unstable if a movement of the user's head is greater than a predetermined threshold. In addition, the first pre-disengagement action may indicate a pressure is released when an absence of pressure on the first user input device or the second user input device is detected. In some aspects, detecting the second pre-disengagement input that indicates a distance change comprises detecting a change in distance between the first user input device and the second user input device that is greater than a distance change that occurs during the teleoperation mode. In some cases, determining whether the position change indicates an unintended pre-disengagement action comprises determining a velocity associated with the position change of the first user input device or the second user input device, and comparing the velocity to a predetermined velocity threshold. In still further aspects, determining whether the position change indicates an unintended pre-disengagement action may include determining an acceleration associated with the position change of the first user input device or the second user input device, and comparing the acceleration to a predetermined acceleration threshold. In addition, determining whether the position change indicates an unintended pre-disengagement action may include determining a jerk associated with the position change of the first user input device or the second user input device, and comparing the jerk to a predetermined jerk threshold. In some cases, the position change may indicate an unintended pre-disengagement action when a velocity, acceleration and jerk associated with the position change exceed a predetermined velocity threshold, acceleration threshold and jerk threshold, respectively. Still further, determining whether the position change indicates an unintended pre-disengagement action further may include comparing a velocity of the first user input device and a velocity of the second user input device, and when the velocities are the same, the position change indicates an unintended user action.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Figure 1:
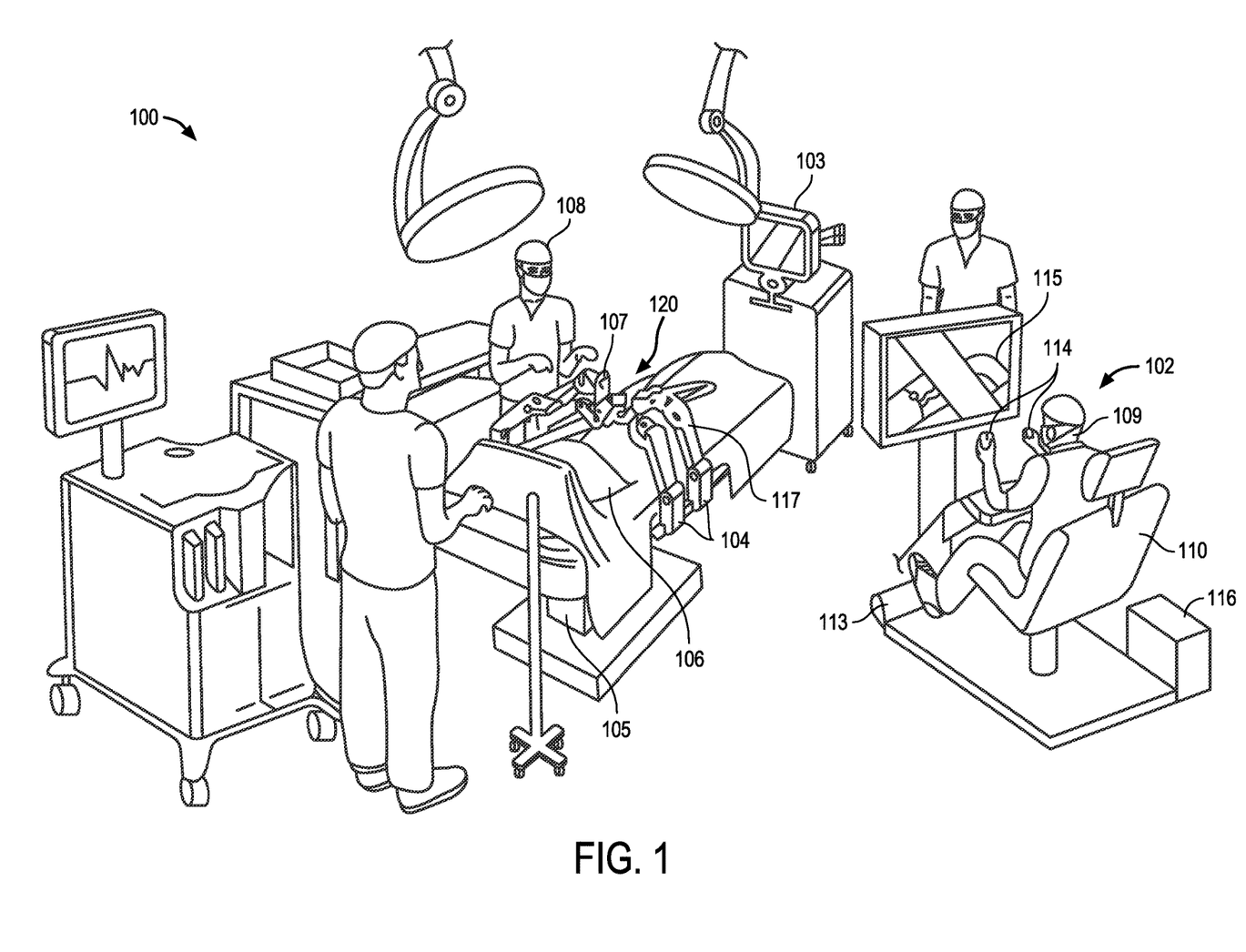
FIG. 1 is a pictorial view of an example surgical robotic system in an operating arena, in accordance with an embodiment.

Referring to FIG. 1, this is a pictorial view of an example surgical robotic system 100 in an operating arena. The surgical robotic system 100 includes a user console 102, a control tower 103, and one or more surgical robots 120, including robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation. The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, one or more user interface devices, for example, foot-operated controls 113 or handheld user input devices (UID) 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104).

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site.) Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. Representatively, in some embodiments, UID 114 may be a portable handheld user input device or controller that is ungrounded with respect to another component of the surgical robotic system. For example, UID 114 may be ungrounded while either tethered or untethered from the user console. The term "ungrounded" is intended to refer to implementations where, for example, both UIDs are neither mechanically nor kinematically constrained with respect to the user console. For example, a user may hold a UID 114 in a hand and move freely to any possible position and orientation within space only limited by, for example, a tracking mechanism of the user console. The UID 114 can generate spatial state signals corresponding to movement of the UID 114, e.g. position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106. When the user is finished controlling the surgical tools with the UIDs 114, the user may dock (i.e.,
store) the UIDs 114 with docking stations or UID holders located on the console 102. For example, the console 102 may include docking stations 130 at each of the left and right arm rests of the chair 110. To dock the UIDs 114, the user may move the left UID 114 to the left docking station 130 and the right UID 114 to the right docking station 130, and place each UID in their respective docking station holder.

In some aspects, the communication between the platform 105 and the user console 102 may be through a control tower 103, which may translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system. It will be appreciated that the operating room scene in FIG. 1 is illustrative and may not accurately represent certain medical practices.

In addition, in some aspects, surgical robotic system 100 may further include one or more tracking mechanisms, devices, components or systems (e.g., trackers, sensors, etc.), that can be used to detect one or more pre-engagement actions or pre-disengagement actions indicating a teleoperation mode should be engaged or, once engaged, should be disengaged. The mechanisms may detect, for example, a movement of the user's head relative to the display 115 or a movement of a UID being held by the user. This information may, in turn, be used to determine whether the movement indicates the user intends to disengage teleoperation mode (e.g., a pre-disengagement action) or continue engagement of a teleoperation mode (e.g., a pre-engagement action). For example, prior to or during a teleoperation mode of the surgical robotic system 100 in which the user is controlling the surgical tool 107 with the UID 114, the user should be looking at the display 115 so they can view the tool movement. When the user decides to dock the UIDs, and sometimes before docking has actually occurred, the user may look away from the display 115 while still holding the UID 114 and controlling the surgical tool 107. This introduces a risk since the user could move the UID 114 and, in turn, unintentionally move the tool 107. Surgical robotic system 100 may therefore also detect these unintended movements (e.g., pre-disengagement actions) so that an unintended operation of the surgical tool 107 with the UID 114 can be prevented. The various detecting mechanisms may be coupled to, in communication with, or otherwise associated with components of, the user console 102, and will be described in more detail in reference to FIG. 2.

It should be understood that "engaging" the teleoperation mode is intended to refer to an operation in which, for example, a UID or foot pedal that is prevented from controlling the surgical instrument, is transitioned to a mode (e.g., a teleoperation mode) in which it can now control the surgical instrument. On the other hand, disengaging the teleoperation mode is intended to refer to an operation which occurs when the system is in a teleoperation mode, and then transitioned to a mode (non-teleoperation mode) in which the UID or foot pedal can no longer control the surgical instrument. For example, teleoperation mode may be disengaged when the system determines that a detected movement is an unintended action or movement by the user.

Figure 2:
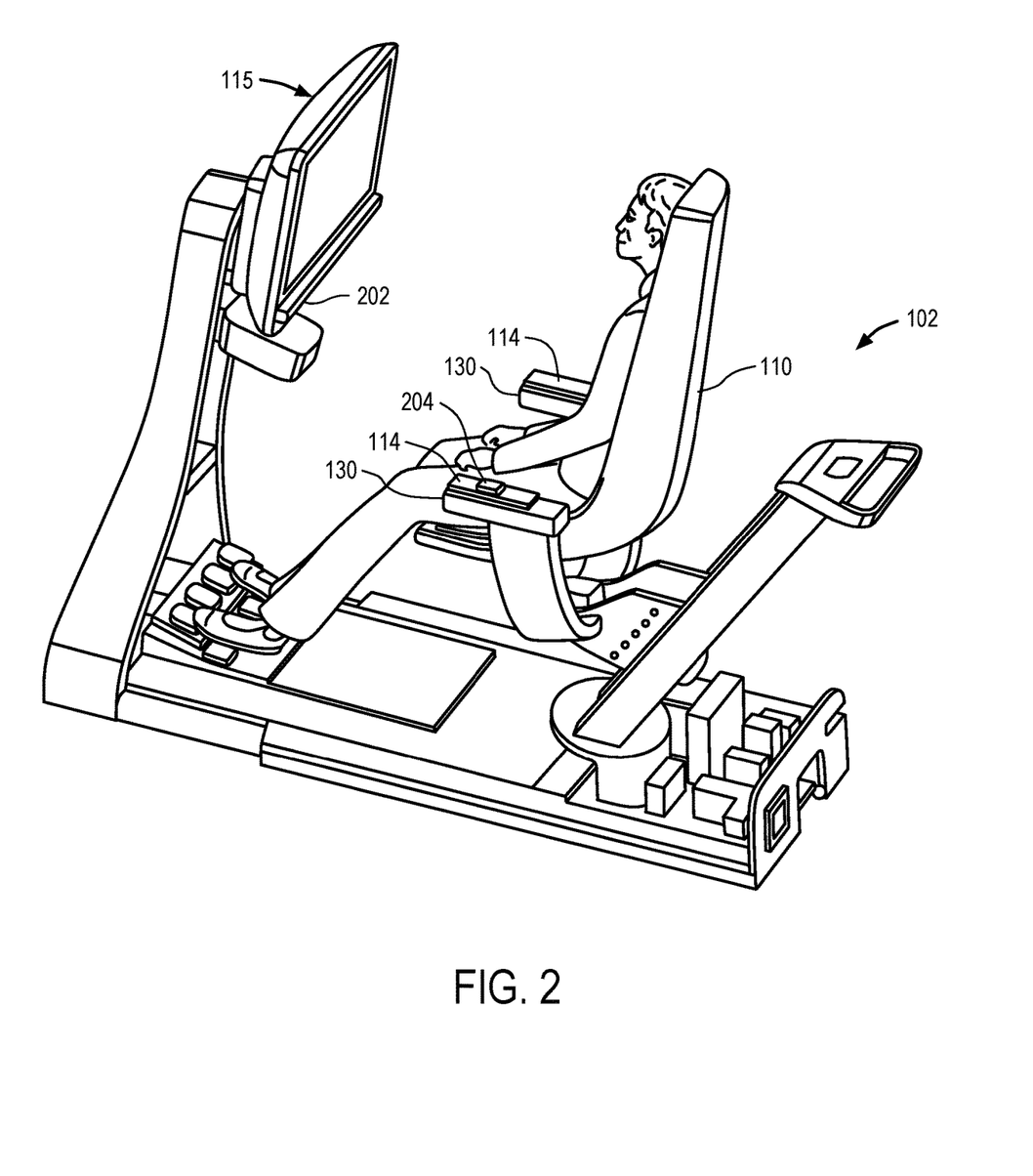
FIG. 2 is a pictorial view of a user console, in accordance with an embodiment.

Referring now to FIG. 2, FIG. 2 illustrates a pictorial view of an exemplary user console including a number of devices, mechanisms, systems and/or components used to detect user actions (e.g., unintended and/or pre-disengagement actions). Representatively, user console 102 is shown including a chair 110 and display 115, as previously discussed. Display 115 may, for example, be an open display. The term "open" display is intended to refer to a display which is designed to allow the user to see outside of the display, for example with their peripheral vision, even when directly facing the display. In addition, in an open display, the user can be a distance from the display screen or not directly in front of the display, and still view a surgical procedure on the display. Therefore, in an open display such as display 115, the fact that the user may not be close to the display or have their face directly in front of the display, would not necessarily mean the user is not looking at the display or focused on the surgical procedure. Rather, in the case of an open display, there will be some tolerance to such actions and allow for teleoperation mode to continue. This is in contrast to an immersive display (e.g., a periscope) that prevents the user from seeing outside of the display screen when they are facing the display and requires the user to be relatively close to the display screen. For example, in the case of an immersive display, the user must have their face relatively close to, and facing, the display screen to use it to view the surgical procedure in progress. If the user pulls their head away from the display screen, or doesn't face the display screen, they can no longer see the display screen, therefore this would typically be interpreted to mean the user is not focused on the screen or not paying sufficient attention to continue in teleoperation mode.

To detect whether the actions of a user at the console are intended or intentional engagement operations (e.g., intended to move a surgical instrument) or unintended or unintentional pre-disengagement operations (e.g., not intended to move a surgical instrument), user console 102 may further include a number of tracking devices, mechanisms, systems and/or components. The tracking mechanisms may include, but are not limited to, a head stability tracker 202, a UID tracker 204, and/or any other tracking device suitable for detecting an action of the user. Each of the tracking mechanisms are configured to detect at least one of a number of actions of the user which may be required to continue, engage or disengage a teleoperation mode. As previously discussed, the actions may correspond to user interactions with the user console that indicate the user is performing an intentional action during a teleoperation mode (e.g., teleoperation should be engaged) or performing an unintentional action while the UID is still controlling a surgical instrument (e.g., teleoperation should be disengaged).

Representatively, the head stability tracker 202 may be coupled to the display 115 and include a camera that can monitor a motion of the user's head. In addition, the head stability tracker 202 may include a sensor which can be used to monitor a gaze (or gaze change) of the user and a distance of a user's head relative to the monitor. For example, the head stability tracker 202 may include a heat or proximity sensor that can determine a distance of the user's head to the monitor. The UID tracker 204 may include one or more sensors that are directly or indirectly associated with the UID and operable to detect characteristics relating to the operation and/or movement of UID 114. For example, the UID tracker 204 may detect contact between the user's hand and the UID or a movement of the UID 114. For example, the UID tracker 204 may include a pressure or grip sensor that can detect a user holding and manipulating the UID 114. The UID tracker 204 may further include a sensor that can track a distance change, position, angle (e.g., orientation) or the like of the UID 114. For example, the UID tracker 204 may include one or more of an EM sensor, inertial measurement unit (IMU) sensor (e.g., accelerometer or gyroscope), or time of flight sensors for detecting a distance change, position and/or angle (e.g., orientation) of the UID. In addition, the UID tracker 204 may be used to determine a velocity, acceleration and/or jerk of the UID 114. In addition, the UID tracker 204 may track both a left UID and a right UID so that the information relating to one UID can be compared to that of the other UID to determine the motion of one UID relative to another UID.

Figure 3:
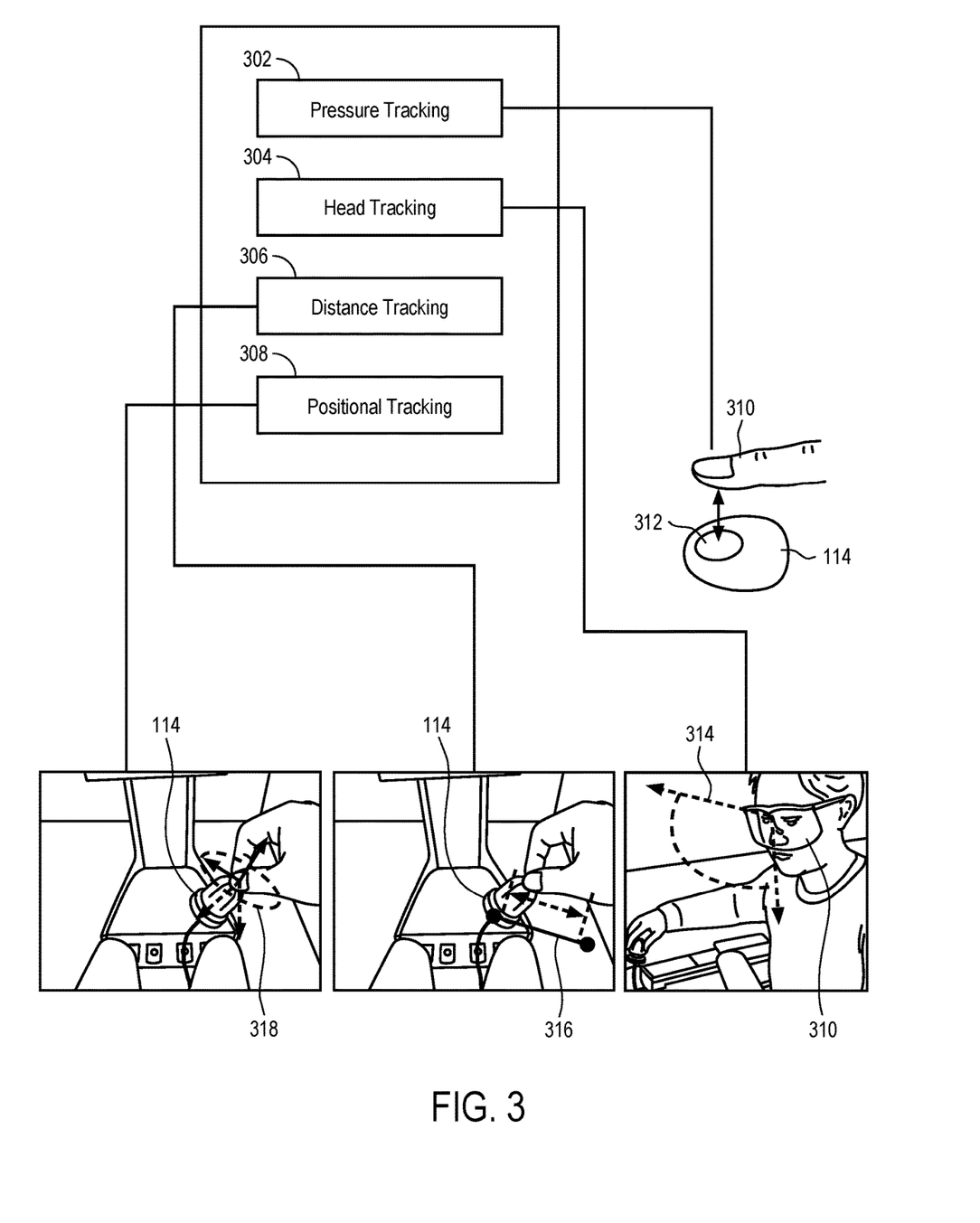
FIG. 3 is a block diagram of an exemplary operation for disengagement detection in accordance with an embodiment.

FIG. 3 is a simplified schematic illustration of the various actions that may be monitored (or tracked) by the tracking devices of FIG. 2. Representatively, the head stability tracker 202 and UID tracker 204 may be used for pressure tracking 302, head tracking 304, positional tracking 306 and/or angular tracking 308 of the user and/or the UID. For example, pressure tracking 302 may include detecting a pressure release or pressure input by the user 310 on a pressure sensor 312 of the UID 114. For example, UID 114 may include a gripping portion including a sensor 312 that a surgeon manipulates using her or his hand (e.g., squeezes), to generate an input command to move an actuator, to which a robotic surgical tool and/or end effector is coupled in the surgical robotic system. The surgeon can squeeze and move the UID 114 within a workspace to remotely cause a corresponding movement of the actuator. Prior to, or during, docking, however, the user will release (or begin to release) their grip on the UID 114. The pressure on the UID 114 may therefore go from at least some pressure on the device to zero pressure on the device. UID tracker 204 may detect the user releasing the UID 114 (e.g., an absence of pressure) prior to docking as an unintended pre-disengagement action. Head tracking 304 may include detecting a movement 314 of the head of the user 310. For example, when the user decides to dock the UID 114 or is docking the UID 114, they may move their head slightly to look at the docking station. This movement can be detected by head tracking 304 as an unintended pre-disengagement action. Distance tracking 306 may include detecting a movement of the UID 114, for example a distance change of one UID relative to another UID. For example, distance tracking 306 may include tracking the UID 114 at one or more positions and/or a distance 316 the UID 114 moves between the positions or relative to another UID. Position tracking 308 may include detecting an orientation of the UID 114 and/or a change in orientation of the UID 114 within a three-dimensional coordinate system 318. For example, a pivot, rotation or the like of the UID 114 relative to the x, y and z axes of coordinate system 318. The information detected by the pressure tracking 302, head tracking 304, positional tracking 308 and angular tracking 308 is then analyzed and compared to various threshold values to determine whether, for example, the user action is an unintended pre-disengagement action and therefore teleoperation should be disengaged to prevent an unintended movement of the associated surgical instrument. For example, in some aspects, if it is determined that a pressure on the UID has been released or the head movement is unstable, and the UID angle and UID position exceed predetermined thresholds (e.g., maximum thresholds for an intended action used to move the surgical instrument), the system may determine the action or movement of the user is an unintended pre-disengagement action (e.g., not intended to move the surgical instrument) and that teleoperation should be disengaged to prevent unintended movement of a surgical instrument.

Figure 4:
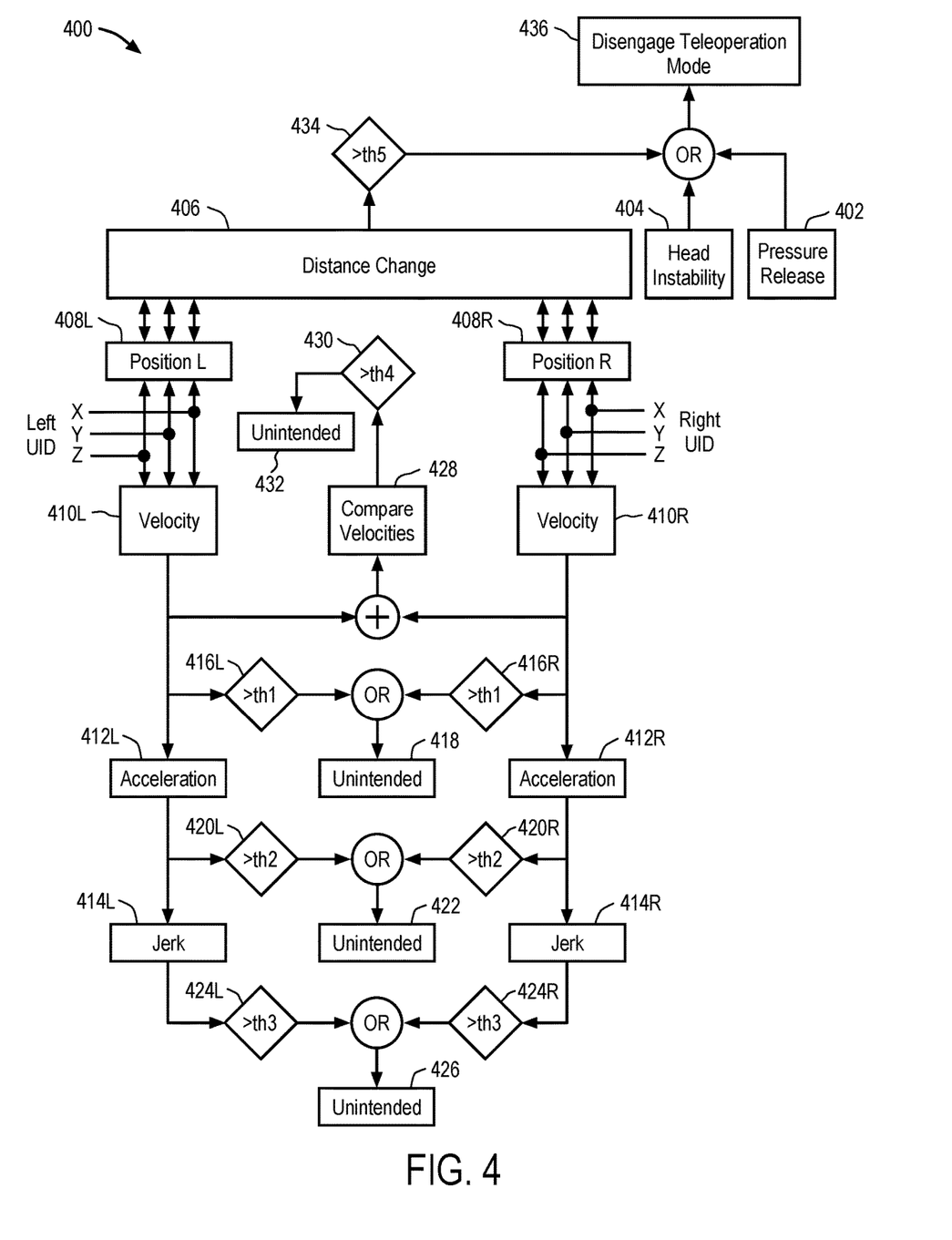
FIG. 4 is a block diagram of an exemplary operation for disengagement detection in accordance with an embodiment.

FIG. 4 is a block diagram of an exemplary process for determining an unintended user action based on the previously discussed data detected by the various sensors and/or tracking mechanisms. Representatively, process 400 may include the initial pre-disengagement operations of detecting a pressure release operation 402 or detecting a head instability operation 404. At least one of operations 402 or 404 must be detected prior to proceeding to distance operation 406. The pressure release operation 402 may include detecting a pressure release on the UID (e.g., UID 114), for example by a pressure sensor associated with the UID, as previously discussed. For example, the sensor may detect an absence of pressure on the UID as an indicator that the user has released their grip on the UID or is no longer squeezing the UID. Such an action typically occurs before docking or during docking therefore the system recognizes this action as an unintended pre-disengagement action or an indicator that the user may be performing, or is about to perform, an unintended action.

The head instability operation 404 may include detecting a movement of the user's head, for example by a head tracking mechanism as previously discussed. Typically, when the user is using the UID to control a surgical instrument, they are looking toward the display and do not move their head or only move their head within a predetermined threshold range. On the other hand, when the user is about to dock, or is docking, the UID, they may look away from the display, for example toward one of the docking stations associated with the console. Accordingly, when the system detects a head movement at operation 404 greater than a predetermined threshold range typically occurring during teleoperation, the system recognizes the movement as a head instability. Representatively, the threshold may be an angular rotation of the head of greater than 0 degrees, for example, about 5 degrees, 10 degrees, 20 degrees, 30 degrees, 40 degrees, 50 degrees, 60 degrees, 70 degrees, 80 degrees, 90 degrees, 100 degrees or more. For example, if the system detects a rotation or movement of the head greater than, for example 5 degrees at operation 404, the system determines a head instability is detected. This head instability is in turn considered an indicator that the user may be performing, or is about to perform, an unintended pre-disengagement action.

Once at least one of a pressure release or head instability are detected at operations 402 or 404, process 400 proceeds to operation 406 where it is determined whether a distance change has occurred between a right UID and a left UID. For example, at operation 406 the system determines whether the distance between the left UID and the right UID has changed, and if so, the change is beyond a predetermined threshold range (e.g., th5) at operation 434. The detection of a distance change is used as another indicator that the user is engaging in an unintended pre-disengagement action that should not be translated to the surgical instrument (e.g., the user is preparing to dock, or is docking, the UIDs). Typically, when the user is using the UIDs to control a surgical instrument, the user holds the left and right UIDs in front of their body and the distance between the left and right UIDs remains relatively unchanged, or within a predetermined threshold range. When the user decides to dock the UIDs, or is in the process of docking the UIDs, they will typically move the right UID to a docking station on the right side of the console and the left UID to a docking station on the left side of the console. Accordingly, prior to and/or during the docking process, the distance between the left and right UIDs changes. When this distance change is detected, or is greater than a predetermined threshold range (e.g., th5) typically occurring between UIDs during teleoperation, the system recognizes the movement as an indicator that the movement of the UID is not intended by the user and/or is not intended to control the associated surgical instrument. The movement is therefore categorized as an unintended pre-disengagement action and based on this determination, the system may disengage teleoperation so that the UID movement does not move the associated surgical instrument.

Several characteristics of the distance change at operation 406 are further analyzed to confirm it is associated with an unintended pre-disengagement operation. For example, a position, a velocity, an acceleration and a jerk associated with the distance change determined at operation 406 is further analyzed at operations 408R-414R and 408L-414L. Operations 408R-414R may evaluate these characteristics in relation to the right UID and operations 408L-414L may evaluate these characteristics relative to the left UID. The characteristics of the right and left UIDs are evaluated individually at 408R-414R and 408L-414L so that even if one UID moves and the other does not, a movement of at least one UID is still detected and analyzed to determine whether an unintended pre-disengagement action has occurred.

Referring now in more detail to operations 408R and 408L, at operations 408R and 408L a position and/or position change of each of the right UID and/or left UID, respectively, is analyzed. For example, at operation 408R a position and/or position change of the right UID is analyzed relative to the x, y and z axes within a three-dimensional space. If a position change is detected, the system further analyzes the velocity, acceleration and jerk associated with the position change at operations 410R-414R and 410L-414L. In particular, at operation 410R, the process analyzes the velocity of the right UID by determining the rate of change of the right UID position with respect to a frame of reference. The velocity of the right UID is then compared to a predetermined velocity threshold (e.g., th1) at operation 416R. The predetermined velocity threshold may be a maximum acceptable velocity of a UID during a teleoperation mode, or a velocity otherwise consistent with a typical positional velocity that occurs during a teleoperation mode. For example, when a surgeon is using the UID to control the surgical instrument during the teleoperation mode, the surgeon's movement of the UID will typically be relatively slow and controlled so that the corresponding movement of the surgical instrument within the body does not damage the tissue. On the other hand, when the surgeon is, for example, docking the UID, the surgeon may change the position of the UID relatively quickly as they are moving the UID toward the docking station. A relatively fast position change of the UID would therefore be more consistent with an action that is not intended to control the surgical instrument, for example, a docking action, as opposed to an action intended to control the surgical instrument. Accordingly, if the positional velocity of the right UID at operation 416R is found to exceed the predetermined velocity threshold (e.g., th1), the system categorizes the action relative to the right UID as an unintended pre-disengagement action at operation 418. Similarly, at operation 410L, the system determines the rate of change of the left UID position with respect to the frame of reference. The positional velocity of the left UID is then compared to a predetermined threshold (e.g., th1) at operation 416L. The predetermined threshold (e.g., th1) for the left UID at operation 416L may be the same as the predetermined threshold (e.g., th1) for the right UID at operation 416R. If the rate of change of the left UID position at operation 416L is found to exceed the predetermined threshold (e.g., th1), the system categorizes the action relative to the left UID as an unintended pre-disengagement action at operation 418. It should be recognized that a position change of the right UID or the left UID which exceeds the threshold will be recognized by the system as an unintended pre-disengagement action at operation 418. In other words, it is not necessary for both the left and right UIDs to change positions, or change positions at a rate greater than the threshold, for the system to conclude a UID position change consistent with an unintended pre-disengagement action has occurred.

The acceleration of the right and left UIDs is further analyzed at operations 412R, 412L. In particular, at operation 412R, the process determines the rate of change of the previously determined velocity of the right UID over time. The acceleration of the right UID is then compared to a predetermined acceleration threshold (e.g., th2) at operation 420R. The predetermined acceleration threshold may be a maximum acceptable acceleration of a UID during a teleoperation mode, or an acceleration otherwise consistent with a typical positional change that occurs during a teleoperation mode. As previously discussed, when a surgeon is using the UID to control the surgical instrument during the teleoperation mode, the surgeon's movement of the UID will typically be relatively slow and controlled so that the corresponding movement of the surgical instrument within the body does not damage the tissue. A relatively quick acceleration of the UID would therefore be more consistent with an action that is not intended to control the surgical instrument, for example, a docking action, as opposed to an action intended to control the surgical instrument. Accordingly, if the acceleration of the right UID at operation 420R is found to exceed the predetermined acceleration threshold (e.g., th2), the system categorizes the action relative to the right UID as an unintended pre-disengagement action at operation 422. Similarly, at operation 412L, the system determines the acceleration of the left UID. The acceleration of the left UID is then compared to a predetermined threshold (e.g., th2) at operation 420L. The predetermined threshold (e.g., th2) for the left UID at operation 420L may be the same as the predetermined threshold (e.g., th2) for the right UID at operation 420R. If the acceleration of the left UID at operation 420L is found to exceed the predetermined threshold (e.g., th2), the system categorizes the action relative to the left UID as an unintended pre-disengagement action at operation 422. It should be recognized that an acceleration of the right UID or the left UID which exceeds the threshold will be recognized by the system as an unintended pre-disengagement action at operation 422. In other words, it is not necessary for both the left and right UIDs to accelerate, or accelerate at a rate greater than the threshold, for the system to conclude a UID acceleration consistent with an unintended pre-disengagement action has occurred.

The jerk of the right and left UIDs is further analyzed at operations 414R, 414L. In particular, at operation 414R, the process determines the rate of change of the previously determined acceleration of the right UID. This jerk value for the right UID is then compared to a predetermined acceleration threshold (e.g., th3) at operation 424R. The predetermined jerk threshold may be a maximum acceptable jerk of a UID during a teleoperation mode, or jerk otherwise consistent with a typical jerk type motion that could occur during a teleoperation mode. During a teleoperation mode, the surgeon will typically avoid jerking the UID, or at least minimize any jerk, therefore a relatively quick jerk of the UID would be more consistent with an action that is not intended to control the surgical instrument, for example, a docking action, as opposed to an action intended to control the surgical instrument. Accordingly, if the jerk of the right UID at operation 424R is found to exceed the predetermined acceleration threshold (e.g., th3), the system categorizes the action relative to the right UID as an unintended pre-disengagement action at operation 426. Similarly, at operation 414L, the system determines the jerk of the left UID. The jerk of the left UID is then compared to a predetermined threshold (e.g., th3) at operation 424L. The predetermined threshold (e.g., th3) for the left UID at operation 424L may be the same as the predetermined threshold (e.g., th3) for the right UID at operation 424R. If the jerk of the left UID at operation 424L is found to exceed the predetermined threshold (e.g., th3), the process categorizes the action relative to the left UID as an unintended pre-disengagement action at operation 426. It should be recognized that a jerk of the right UID or the left UID which exceeds the threshold will be recognized by the system as an unintended pre-disengagement action at operation 426. In other words, it is not necessary for both the left and right UIDs to experience a jerk, or a jerk greater than the threshold, for the system to conclude a UID jerk consistent with an unintended pre-disengagement action has occurred.

In addition, process 400 may include operation 428 which compares the velocities determined at operations 410R and/or 410L to remove any false positives. In particular, the velocities determined at operations 410R and/or 410L can be compared to determine whether they are the same or relatively the same, before concluding an unintended pre-disengagement action has occurred. Typically, prior to docking, or during docking, the velocity of the left and right UIDs will be relatively the same since the surgeon is performing the same task with each UID (e.g., moving the UID to the associated docking station). On the other hand, during teleoperation, the left and the right UIDs may be used to perform different operations therefore the velocities of each UID will typically not be the same, or will not be substantially the same. Thus, if the velocities determined at operations 410R and 410L are the same, or substantially the same, the process can use this information as a further indicator that the actions of the left and right UIDs are consistent with an unintended pre-disengagement action at operation 422. To determine whether the velocities determined at operations 410R and 410L are substantially the same, any difference between the velocities of the left UID and the right UID can be compared to a predetermined comparison threshold (e.g., th4) at operation 430. The predetermined comparison threshold (e.g., th4) may correspond to an acceptable velocity difference between left and right UIDs that could occur, or a velocity difference that has been found to occur, during a surgical procedure in the teleoperation mode. If the difference between the velocities of the left and right UIDs is found to exceed the threshold at operation 430, the process categorizes the action as an unintended pre-disengagement action at operation 432.

If the pressure release operation 402 or the head instability operation 404, and the distance change operation 406 (e.g., the velocity, acceleration and jerk of at least one UID exceeds the predetermined thresholds) are all found to be consistent with an unintended pre-disengagement action, the process determines the user is engaging in an unintended pre-disengagement action. Once an unintended pre-disengagement action is determined, the UID is prevented from controlling the surgical instrument by disengaging the teleoperation mode at operation 436.

It should be understood that the data used to perform each of the operations of process 400 may be continuously collected by any one or more of the previously discussed sources (e.g., head stability tracker 202 and UID tracker 204) and the operations continuously performed so that unintended pre-disengagement actions can be detected, and teleoperation disengaged, immediately. For example, the various sources may collect the data at least every millisecond, and the operations of process 400 may be performed as soon as the data is collected. In this aspect, the system is able to detect the unintended pre-disengagement actions and disengage teleoperation as soon as it happens, or/and before, for example, the surgeon docks the UIDs. In this aspect, the system can automatically disengage teleoperation to prevent any docking related actions of the user while holding the UIDs from causing an unintended movement of the associated surgical instrument.

Figure 5:
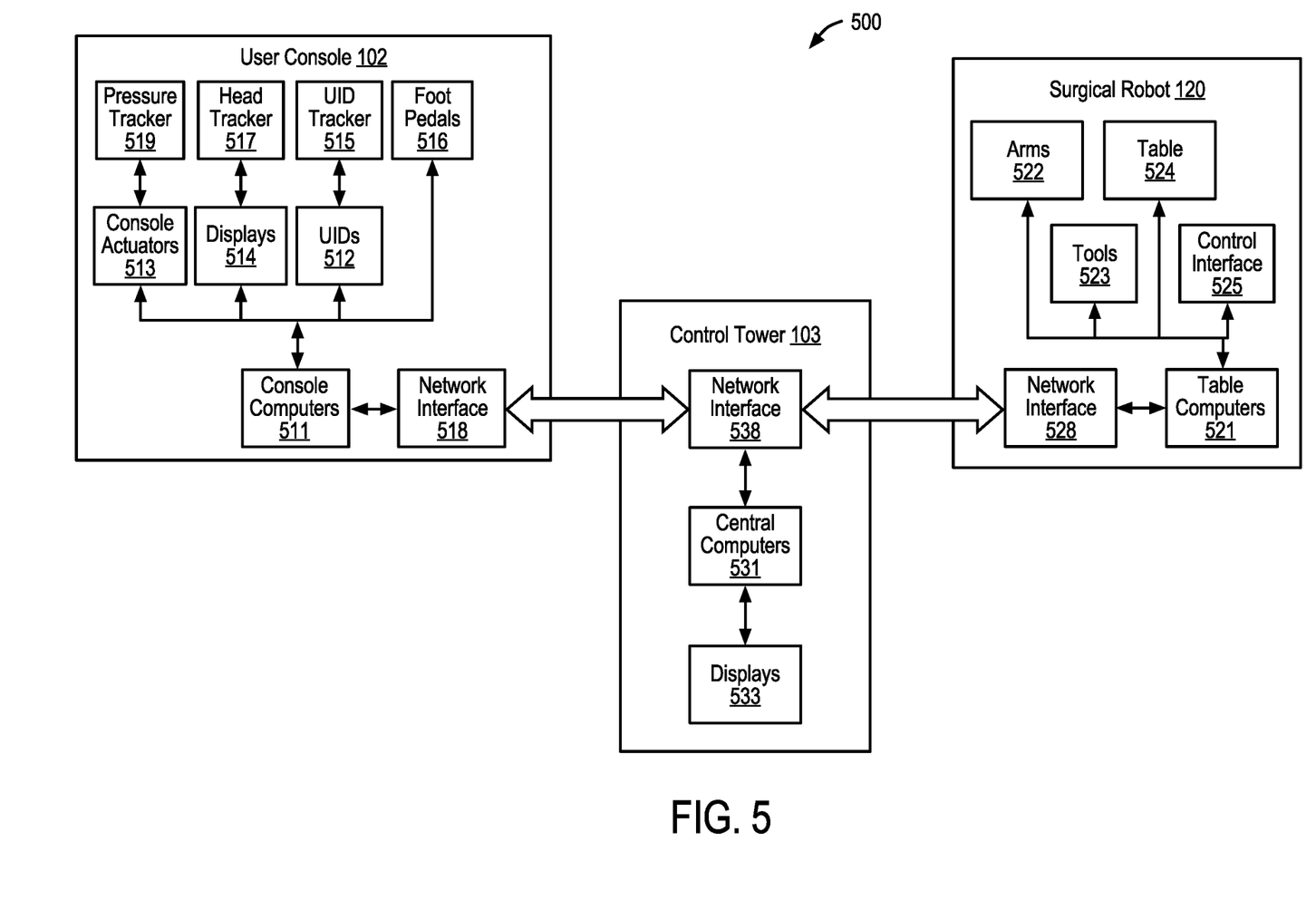
FIG. 5 is a block diagram of a computer portion of a user console including interlock mechanisms, in accordance with an embodiment.

FIG. 5 is a block diagram of a computer portion of a surgical robotic system, which is operable to implement the previously discussed operations, in accordance with an embodiment. The exemplary surgical robotic system 500 may include a user console 102, a surgical robot 120, and a control tower 103. The surgical robotic system 500 may include other or additional hardware components; thus, the diagram is provided by way of example and not a limitation to the system architecture.

As described above, the user console 102 may include console computers 511, one or more UIDs 512, console actuators 513, displays 514, foot pedals 516, console computers 511 and a network interface 518. In addition, user console 102 may include a number of tracking mechanisms, devices, or components, for example, a UID tracker(s) 515, a head tracker(s) 517 and a pressure tracker(s) 519 for detecting pre-disengagement actions of a user as previously discussed. For example, pressure tracker(s) 519 may include any one or more of the previously discussed UID sensors, for example, a sensor for detecting a pressure release of the user on the UID. UID tracker(s) 515 may include an EM sensor, inertial measurement unit (IMU) sensor (e.g., accelerometer or gyroscope), or time of flight sensors for detecting a distance change, position and/or angle (e.g., orientation) of the UID. Head tracker(s) 517 may include one or more sensors for detecting a head instability. The information detected and/or tracked by any one or more of the trackers may be monitored and communicated to the console computer 511, and dispatched to the control tower 103 via the network interface 518, so that the system can determine whether a detected action is an unintended pre-disengagement action and whether to engage and/or disengage a teleoperation mode.

It should further be understood that a user or surgeon sitting at the user console 102 can adjust ergonomic settings of the user console 102 manually, or the settings can be automatically adjusted according to user profile or preference. The manual and automatic adjustments may be achieved through driving the console actuators 513 based on user input or stored configurations by the console computers 511. The user may perform robot-assisted surgeries by controlling the surgical robot 120 using one or more master UIDs 512 and foot pedals 516. Positions and orientations of the UIDs 512 are continuously tracked by the UID tracker 515, and status changes are recorded by the console computers 511 as user input and dispatched to the control tower 103 via the network interface 518. Real-time surgical video of patient anatomy, instrumentation, and relevant software apps can be presented to the user on the high resolution 3D displays 514 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly-adjustable seat for surgeons and master UIDs tracked through electromagnetic or optical trackers are included at the user console 102 for improved ergonomics.

The control tower 103 can be a mobile point-of-care cart housing touchscreen displays, computers that control the surgeon's robotically-assisted manipulation of instruments, safety systems, graphical user interface (GUI), light source, and video and graphics computers. As shown in FIG. 5, the control tower 103 may include central computers 531 including at least a visualization computer, a control computer, and an auxiliary computer, various displays 533 including a team display and a nurse display, and a network interface 518 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 may include an articulated operating table 524 with a plurality of integrated arms 522 that can be positioned over the target patient anatomy. A suite of compatible tools 523 can be attached to or detached from the distal ends of the arms 522, enabling the surgeon to perform various surgical procedures. The surgical robot 120 may also comprise control interface 525 for manual control of the arms 522, table 524, and tools 523. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 522 includes four arms mounted on both sides of the operating table 524, with two arms on each side. For certain surgical procedures, an arm mounted on one side of the table can be positioned on the other side of the table by stretching out and crossing over under the table and arms mounted on the other side, resulting in a total of three arms positioned on the same side of the table 524. The surgical tool can also comprise table computers 521 and a network interface 518, which can place the surgical robot 120 in communication with the control tower 103.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method for disengagement detection of a surgical instrument of a surgical robotic system, the method comprising:

detecting a gaze change of a user prior to disengagement of a teleoperation mode;

detecting a pressure change input relative to at least one of a first user input device or a second user input device for controlling a surgical instrument of the surgical robotic system during the teleoperation mode; and detecting a position change of the first user input device or the second user input device and determining whether a velocity of the position change indicates the user is performing an unintended action prior to disengagement of the teleoperation mode.

2. The method of claim 1 wherein the gaze change is detected by a head tracking device.

3. The method of claim 1 wherein the detecting the pressure change input comprises detecting a pressure release on the first or second user input device by a pressure sensor.

4. The method of claim 1 wherein the velocity of the position change indicates the user is performing the unintended action when the velocity exceeds a predetermined disengagement threshold.

5. The method of claim 1 wherein detecting the position change further comprises determining an acceleration or a jerk of the first user input device or the second user input device, and comparing the acceleration or the jerk to a predetermined disengagement threshold.

6. The method of claim 5 wherein the predetermined disengagement threshold comprises a velocity threshold, an acceleration threshold and a jerk threshold that correspond to a maximum velocity, a maximum acceleration and a maximum jerk occurring during the teleoperation mode, respectively.

7. The method of claim 1 wherein determining the velocity comprises comparing a velocity of the first user input device and a velocity of the second user input device, and when the velocities are the same, determining the position change indicates the user is performing the unintended action.

8. The method of claim 1 further comprising, in response to determining the user is performing the unintended action prior to disengagement of the teleoperation mode, disengage the teleoperation mode such that the first user input device and the second user input device are prevented from controlling the surgical instrument.

9. The method of claim 1 wherein the unintended action prior to disengagement of the teleoperation mode comprises an action by the user relative to the first user input device or the second user input device that is not intended to cause a movement of an associated surgical instrument.

10. A method for disengagement detection of a surgical instrument of a surgical robotic system, the method comprising:

detecting a first pre-disengagement action that corresponds to a user action prior to disengagement of a teleoperation mode;

in response to detecting the first pre-disengagement action, detecting a second pre-disengagement action that indicates a position change of a first user input device or a second user input device;

in response to detecting the second pre-disengagement action, determine whether a velocity of at least one of the first user input device or the second user input device associated with the position change indicates the user action is an unintended pre-disengagement action; and in response to determining the user action is an unintended pre-disengagement action, disengage the teleoperation mode such that the first user input device and the second user input device are prevented from controlling the surgical instrument.

11. The method of claim 10 wherein the first pre-disengagement action comprises a user gaze change indicating a user's head is unstable.

12. The method of claim 10 wherein the first pre-disengagement action comprises a rotation of a user's head greater than five degrees.

13. The method of claim 10 wherein the first pre-disengagement action comprises a change in a distance between a user's head and a monitor of the surgical robotic system.

14. The method of claim 10 wherein the first pre-disengagement action comprises a pressure change relative to at least one of a first user input device or a second user input device.

15. The method of claim 14 wherein detecting the pressure change comprises a sensor coupled to the first user input device or the second user input device detecting an absence of pressure on the first user input device or the second user input device.

16. The method of claim 10 wherein detecting the second pre-disengagement action that indicates the position change comprises detecting a change in distance between the first user input device and the second user input device that is greater than a distance change that occurs during the teleoperation mode.

17. The method of claim 10 wherein determining the velocity indicates the user action is an unintended pre-disengagement action comprises comparing the velocity to a predetermined velocity threshold and determining the velocity exceeds the predetermined velocity threshold.

18. The method of claim 10 wherein determining whether the position change indicates the unintended pre-disengagement action further comprises determining an acceleration associated with the position change of the first user input device or the second user input device, and comparing the acceleration to a predetermined acceleration threshold.

19. The method of claim 10 wherein determining whether the position change indicates the unintended pre-disengagement action further comprises determining a jerk associated with the position change of the first user input device or the second user input device, and comparing the jerk to a predetermined jerk threshold.

20. The method of claim 10 wherein determining whether the position change indicates the unintended pre-disengagement action comprises comparing the velocity of the first user input device and the velocity of the second user input device, and when the velocities are the same, the position change indicates an unintended pre-disengagement action.

* * * * *